(12) United States Patent
Edwards

(10) Patent No.: US 7,383,603 B2
(45) Date of Patent: Jun. 10, 2008

(54) FLEXIBLE NECK TOOTHBRUSH

(75) Inventor: Steven J. Edwards, Laguna Niguel, CA (US)

(73) Assignee: Fitmouth, Inc., Laguna Niguel, CA (US)

(*) Notice: Subject to any disclaimer, the term of this patent is extended or adjusted under 35 U.S.C. 154(b) by 823 days.

(21) Appl. No.: 10/721,635

(22) Filed: Nov. 25, 2003

(65) Prior Publication Data

US 2005/0108841 A1    May 26, 2005

(51) Int. Cl.
*A46B 1/00* (2006.01)
(52) U.S. Cl. .................. 15/185; 15/167.1; 15/144.1
(58) Field of Classification Search ............... None
See application file for complete search history.

(56) References Cited

U.S. PATENT DOCUMENTS

| | | | |
|---|---|---|---|
| 2,083,217 A | 6/1937 | Brothers |
| 5,248,113 A | 9/1993 | Daniels |
| 5,467,494 A | 11/1995 | Muller et al. |
| 5,493,747 A | 2/1996 | Inakagata et al. |

(Continued)

FOREIGN PATENT DOCUMENTS

| | | |
|---|---|---|
| DE | 3805326 | 2/1988 |
| DE | 3921371 C1 | 6/1989 |
| JP | 52037150 | 3/1977 |
| WO | WO8910076 | 11/1989 |
| WO | WO 98/37788 | 9/1998 |
| WO | WO 99/39610 | 8/1999 |

OTHER PUBLICATIONS

"The Alert Toothbrush" http://www.saveyoursmile.com/alert/alertfeatures.html, Jun. 15, 2003.

*Primary Examiner*—David Redding
(74) *Attorney, Agent, or Firm*—Stetina Brunda Garred & Brucker

(57) ABSTRACT

All embodiments of the present invention relate to a toothbrush to prevent tooth abrasion and gum damage during use. A first embodiment of the invention includes a handle including an open cavity and a neck interconnected to the handle by a pivot. The neck is movable between an aligned first position and a second angled position relative to the handle. A leaf spring is bonded to the end of the neck at a first end, and the second end of the leaf spring engages the handle to provide biasing resistance. The leaf spring is configured such that if pressure to the neck exceeds a threshold limit, there is movement of the neck portion from the first position to a second position. The threshold limit is the pressure just below the pressure at the brush that may cause damage to the hard and soft tissue of the mouth. A protective sheath envelops the junction between the handle member and the neck member to prevent accumulation of unwanted material within the cavity of the handle. A second embodiment is equivalent in structure and components to the first embodiment except that it also includes a manual adjustment of the biasing force of the leaf spring to provide variable pressure and a motor for providing mechanical movement of the brush head. Third and fourth embodiments are equivalent in structure and components of the first and second embodiments, respectively, except that the leaf spring is bonded to the handle instead of the neck.

17 Claims, 11 Drawing Sheets

U.S. PATENT DOCUMENTS

| | | |
|---|---|---|
| 5,784,742 A | 7/1998 | Giuliani et al. |
| 5,815,872 A | 10/1998 | Meginniss, III et al. |
| 5,898,967 A | 5/1999 | Wu et al. |
| 5,901,397 A | 5/1999 | Hafele et al. |
| 6,081,957 A | 7/2000 | Webb |
| 6,108,869 A | 8/2000 | Meessmann et al. |
| 6,116,784 A | 9/2000 | Brotz |
| 6,327,734 B1 | 12/2001 | Meginniss, III et al. |
| 6,353,958 B2 | 3/2002 | Weihrauch |
| 6,367,112 B1 | 4/2002 | Moskovich et al. |
| 6,374,978 B1 | 4/2002 | Spencer |
| 6,423,098 B1 | 7/2002 | Biedermann |
| 6,425,295 B1 | 7/2002 | Meginniss |
| 6,502,272 B1 | 1/2003 | Fox et al. |
| 6,528,110 B2 | 3/2003 | Szalony |
| 6,536,068 B1 | 3/2003 | Yang et al. |
| 6,543,589 B2 | 4/2003 | Anderson |
| 6,557,662 B1 | 5/2003 | Andonian et al. |
| 2002/0170145 A1 | 11/2002 | Stvartak et al. |

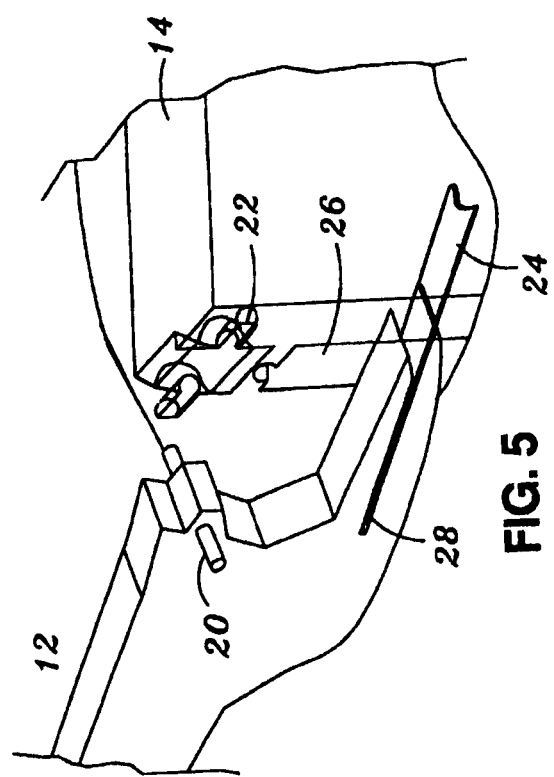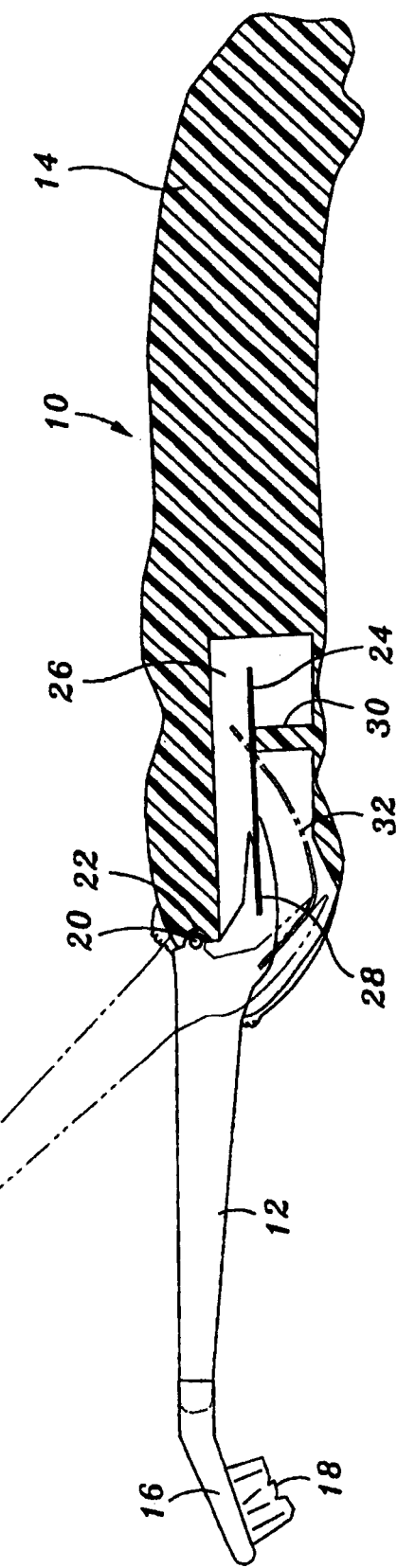

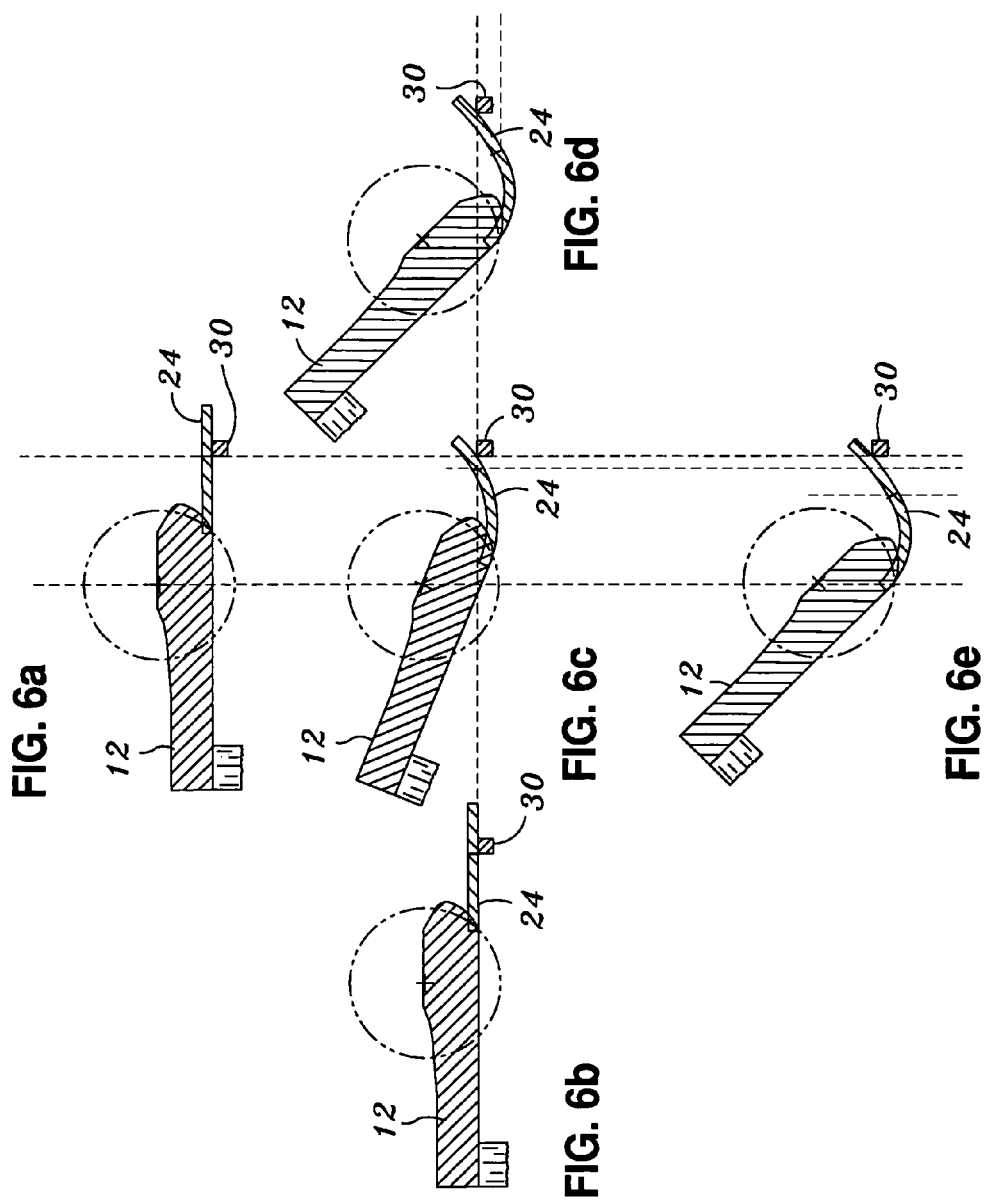

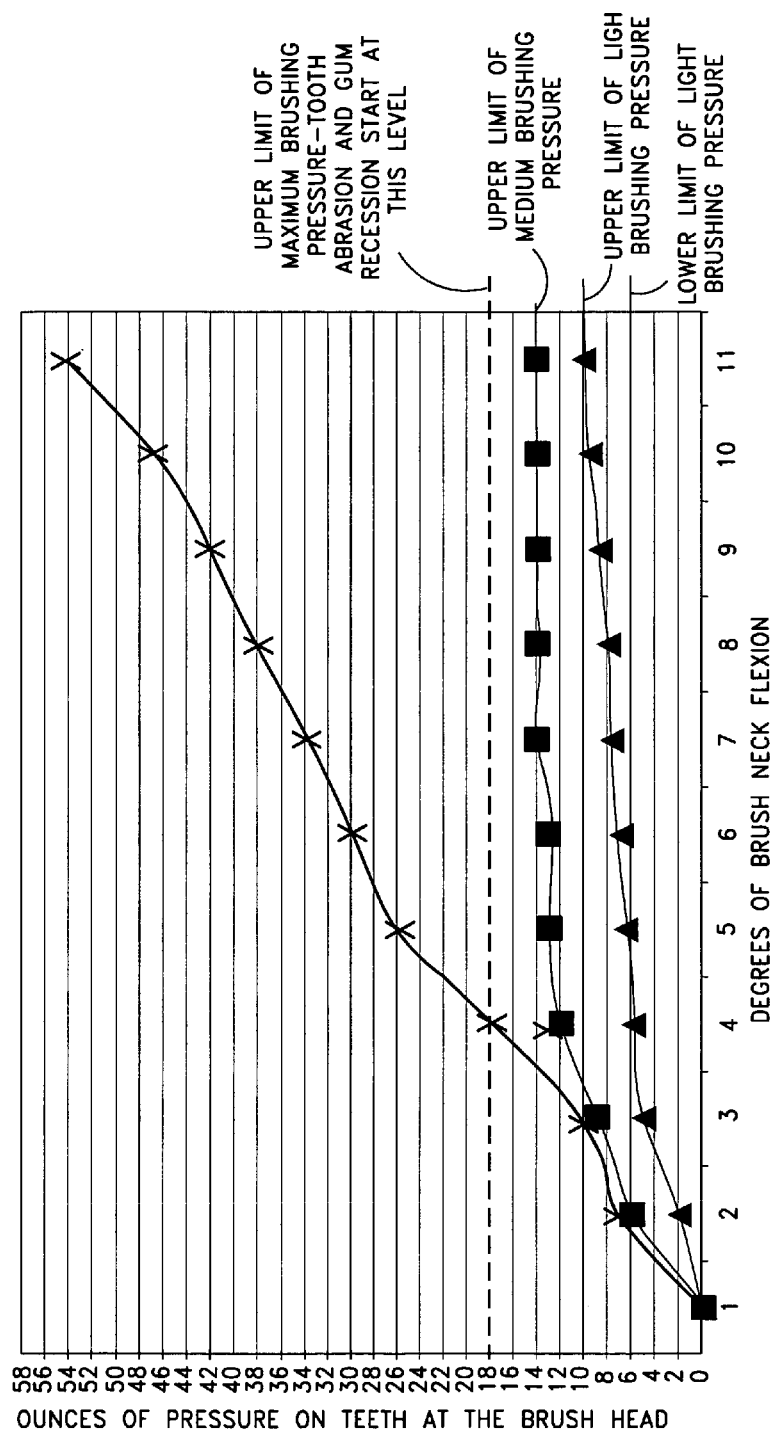

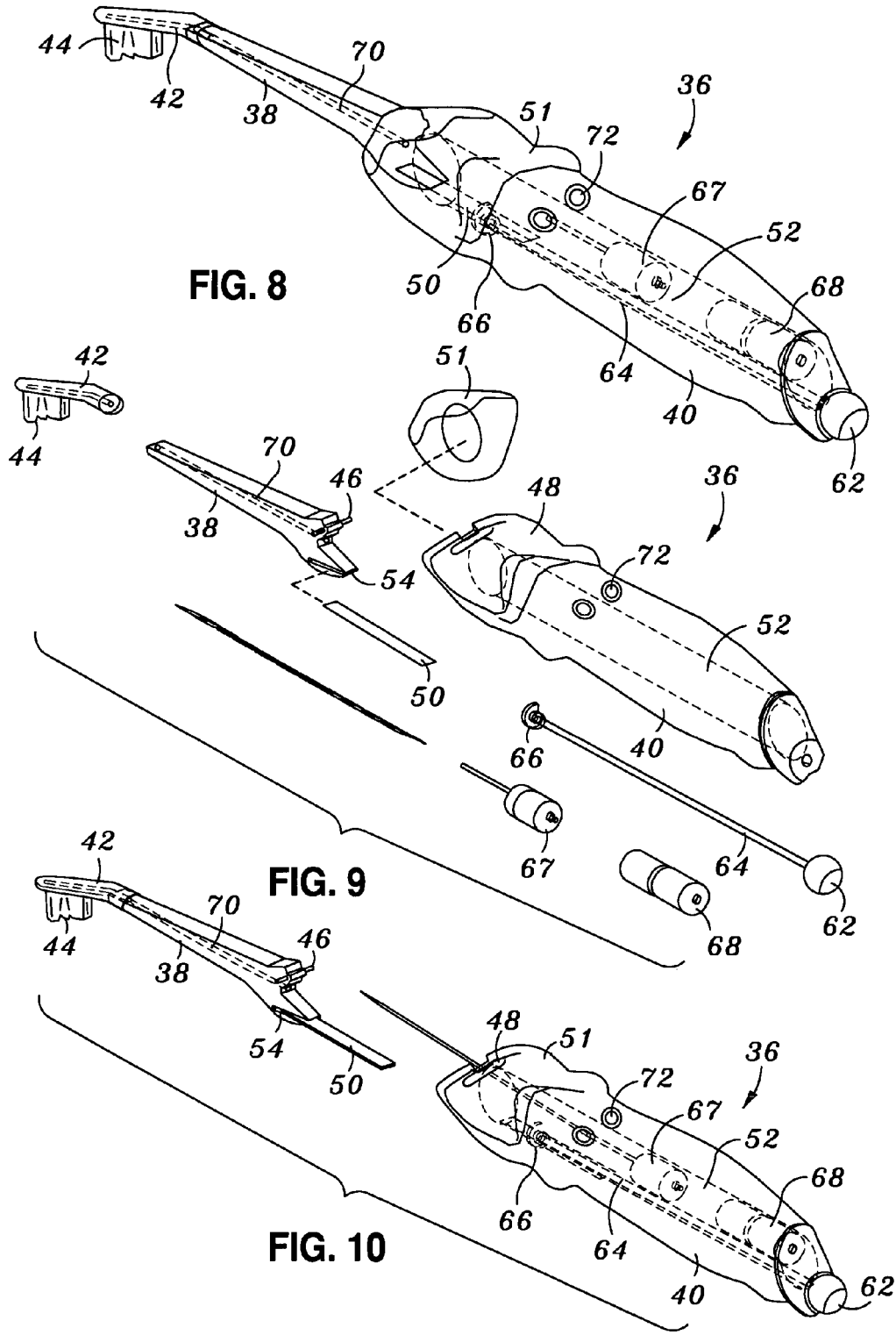

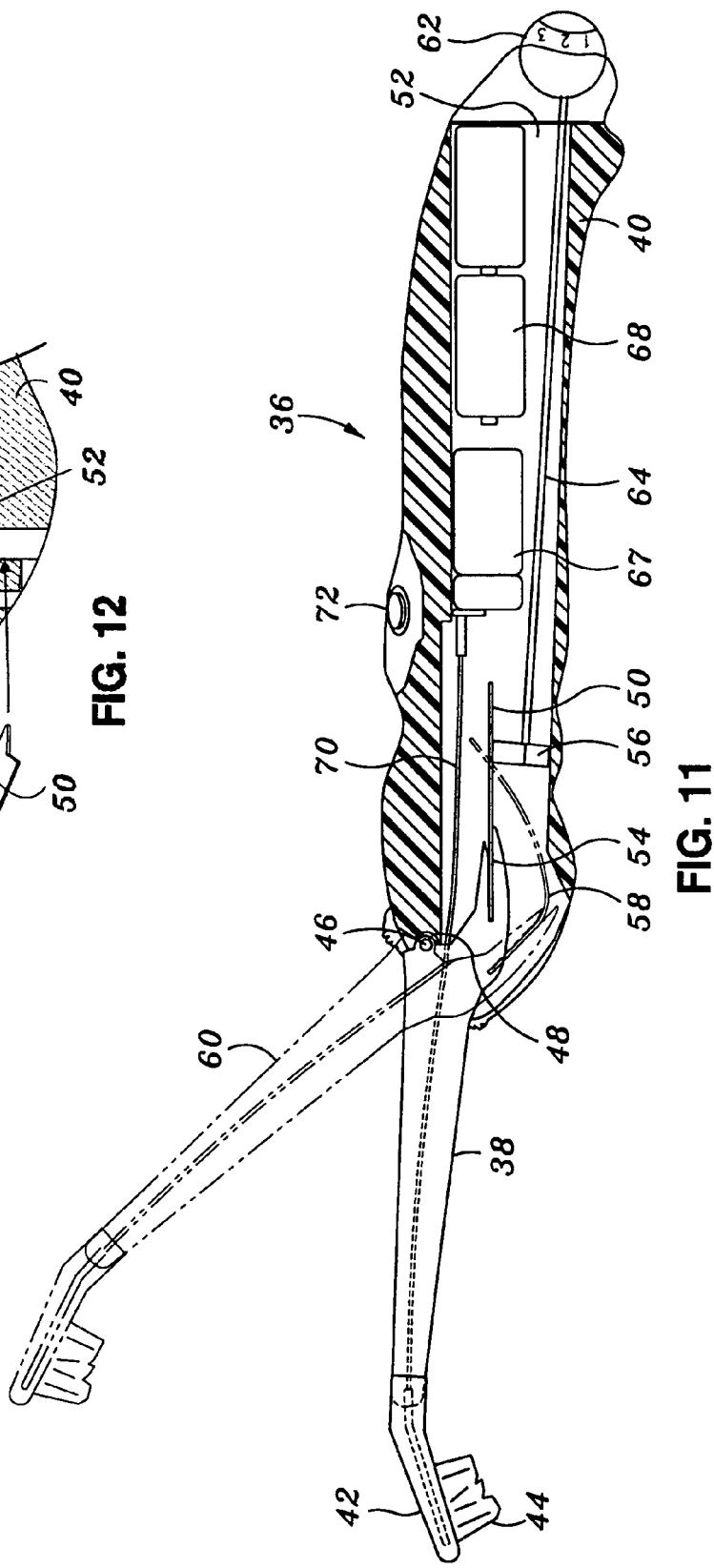
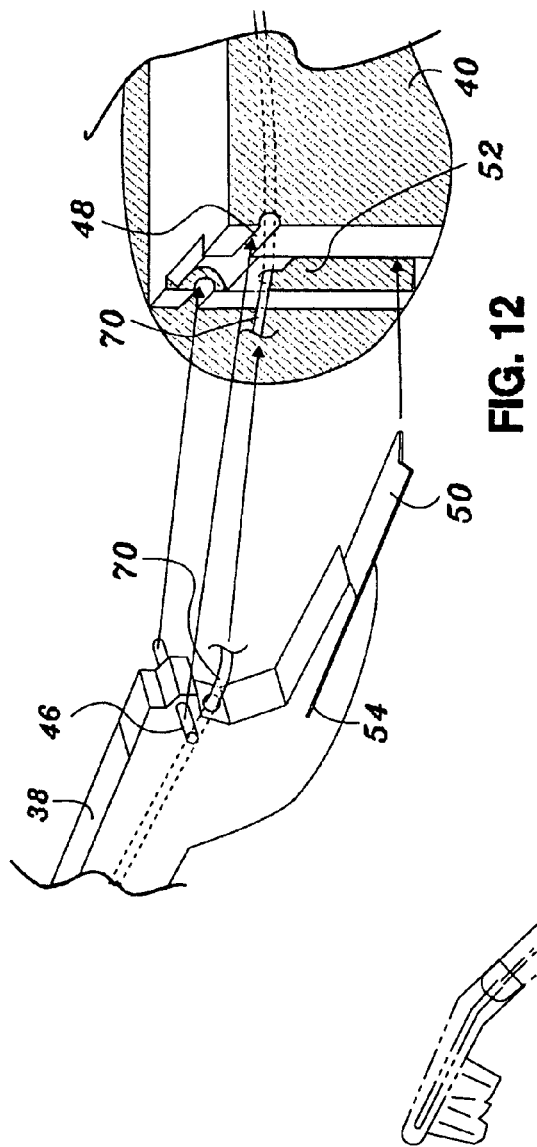
FIG. 11
FIG. 12

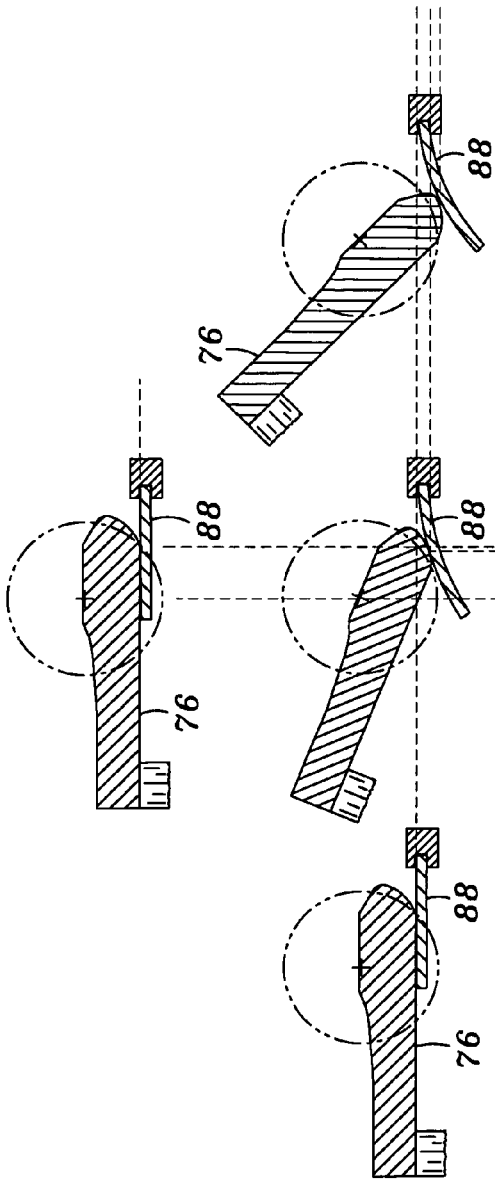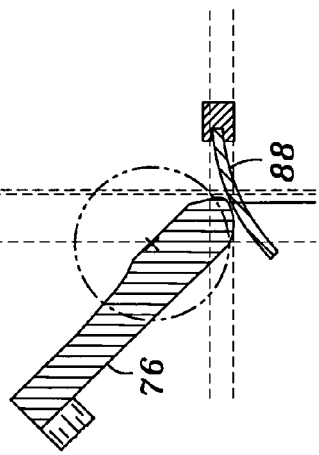

FLEXIBLE NECK TOOTHBRUSH

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

The present invention relates generally to a dental hygiene product namely a flexible neck toothbrush. More particularly, the present invention relates to a toothbrush having a handle portion pivotally connected to a neck portion having a dental brush. A leaf spring, interconnected between the handle portion and the neck portion, allows the neck portion to pivot when a threshold pressure is exceeded on the face of the dental brush. The threshold pressure is a pressure upon the dental brush just below that which causes tooth abrasion and gum damage.

Dental disease is one of the most common human medical afflictions. In an attempt to combat dental disease, the brushing of teeth has become a common daily personal hygiene routine. Many people, however, brush their teeth in an improper fashion by applying excessive pressure to the brush which often damages teeth and gums. Excessive brushing force can cause recession and wear of the gums and other soft oral tissues as well as depletion of hard tissues such as tooth enamel, dentin and cementum. Accordingly, it is desirable to brush the teeth with a light pressure and proper bristle orientation to avoid damage to the hard and soft tissues of the mouth.

Improper and overzealous oral hygiene often leads to severe tooth root abrasion and gum recession, resulting in a domino effect of sensitive teeth, avoidance of brushing, root caries, gum problems, pulpal trauma, root canal therapy, weakened teeth, tooth breakage and eventual tooth loss. Even standard home oral hygiene recommendations and equipment can lead and often do contribute to tooth and gum trauma because of a toothbrush user's inability to adapt use of the toothbrush to the arch curvature of the teeth and gums. Most of the focus in the history of tooth brushing has been directed to brush heads, bristles and toothpaste. Recently, the problem with the use of excessive force from the dental brush upon the teeth has been gaining notoriety. While there has been gaining emphasis on improved safety for brushing, prior safety improvements unsatisfactorily added to the cost of the daily dental hygiene, when it is recognized that the average consumer does not typically spend more than a few dollars on a daily use toothbrush. Thus, there is a great need in the art for improved, ergonomic, safer and cost effective brushing devices which allow controlled forces upon the dentition and supporting structures, as well as aiding in the proper orientation of the toothbrush and contacting bristles.

An acceptable range of pressure used during brushing that is not deleterious to the teeth or gums is known. It is difficult, however, without complex pressure sensing equipment to monitor the pressure applied on the brush against the teeth to stay within the acceptable range of pressure. Prior art devices have attempted to address the use of excessive force and pressure at the brush head by providing pressure-sensing devices. In such devices, when a threshold pressure is reached, an electrical signal is produced and an alarm may sound, a light may flash, a vibration may occur, or the toothbrush neck may disengage. Such pressure sensors and biofeedback systems are typically complex and cannot be produced at a price point level that is acceptable to the average consumer. Another force sensing system such as embodied in U.S. Pat. No. 6,327,734 provides a non-electronic means of feedback by providing a snapping sound when excessive force is applied. The feedback simply provides notice that the safe pressure has been exceeded; however, such feedback may be simply ignored by the user.

As is known in the art, other devices have attempted to address reduction of pressure upon the teeth by providing spring-like flexion within the toothbrush neck or base immediately adjacent the dental brush. In the known prior art, these devices typically create increasing torque as the neck, brush and head remain virtually the same distance apart from the handle, and there is only a slight flexion which mitigates the forces, but does not alleviate the problem of over-pressurization because the slight flexion exhibits Hookian spring characteristics. Hookian spring characteristics are defined by Hooke's law of springs which states that the spring force increases in direct proportion to the distance of displacement of the spring.

Current flexible neck toothbrush designs contribute to tooth abrasion and gum recession because brush head pressure increases directly with handle pressure. Electric toothbrushes were designed to remove more plaque with less force than manual brushes; however, many people utilize automatic toothbrushes just as incorrectly as manual brushes by over pressurization which may have a more deleterious effect than a standard toothbrush because of the added motion or vibration of the brush head.

Other prior art devices additionally include elastomer or other rubber like substances sandwiched between links in the brush neck. Many such prior art devices that utilize very soft elastomer aid in reducing brushing trauma but such devices deform too quickly, and take a significant amount of time (minutes to hours) to reset back to normal. Such brushes can be frustrating to the user because during the proper two-minute brushing interval, such brushes can quickly become deformed out of the ideal shape for proper usage. Other types of toothbrush components employing stiffer elastomers result in increasing torque and increasing force consistent with Hookian principles.

Other prior art devices employ biofeedback, which users often ignore, and such devices involve very complicated sliders, pivots and springs to aid in maintaining consistent force. Such devices, however, appear to be valid only over a very small range of motion and further appear to be too complex for simple daily use. Other prior art devices snap out of place at a predetermined threshold force. It appears that such prior art devices might be clumsy and frustrating to use and users may encounter problems if the devices snap back into place.

In each of the prior toothbrushes, the mechanical attempts to mitigate the excessive force of the brush on the teeth fail for the following reasons, among others: 1). The Hookian spring action of "flexible" toothbrush necks causes increasing brush head force with increasing handle force; 2). Inadequate range of motion wherein the neck flexibly occurs over so small a range of motion as to be easily overruled by excessive handle force and improper brushing motions; 3). Excessive flexibility and poor resetting characteristics which allow the brushes to quickly and progressively bend out of shape while taking minutes or hours for resetting; and/or 4). Poor ergonomics which leads to instability, poor gripping, improper brushing, and tissue damage. Thus, there is a great need in the art for a toothbrush which will automatically maintain a physiologically healthy constant brush head force despite widely varying brush handle forces, positions and motions. Further, there is a great need in the art for a toothbrush that can automatically accommodate variations in dental arch structure and curve alignment as well as variations in manual dexterity without the need for complex sensors and biofeedback mechanisms. There is also a great need in the art for a toothbrush which can provide a constant light pressure on the teeth for people with sensitive gums, gum surgery, oral wounds or other oral maladies. There is also a great need in the art for a user-adjustable variable pressure setting that allows one brush to be multifunctional from ultra soft, to soft, to medium, over an infinite range, or with discrete digital increments between to endpoint settings such that one brush can be used for multiple purposes with a single brush accommodating all types of users. Also needed is a brush that is ergonomic and easy to manipulate and orient properly against dental structures. Consumers would thus benefit from the simplicity of a single brush for use over a wide range of pressures to avoid confusion in the shopping experience and to further avoid the clutter and expense of multiple brushes.

BRIEF SUMMARY OF THE INVENTION

The present invention relates to an ergonomic toothbrush having a flexible neck and adaptively designed handle to prevent tooth abrasion and gum damage during use. A first embodiment of the present invention includes a handle member including an open cavity defining an interior surface. A neck member is interconnected to the handle member via a pivot, wherein the neck member is movable between a first position wherein the handle member and neck member are substantially aligned, and a second position wherein the neck member is angularly offset relative to the handle member. The angle offset can range anywhere from one to forty-five degrees. A leaf spring is bonded at a first end to the end of the neck member, and the second end of the leaf spring engages the interior surface of the handle member to provide biasing resistance. Thus, movement of the neck relative to the handle member about the pivot causes the leaf spring to engage the interior surface of the handle member providing biasing resistance against further pivotal movement. The leaf spring is operative to normally bias the neck member to the first position in substantial alignment with the handle member and is configured such that the application of pressure to the neck portion beyond a prescribed threshold limit causes movement of the neck portion from the first position toward a second position. The neck member is therefore movable between an aligned first position and a second offset position relative to the handle member when a threshold pressure is exceeded. Thus, when the threshold pressure is reached, the biasing member deflects allowing the neck member to move toward a position that is safer or unusable for the user. The threshold pressure is the pressure just below the pressure upon the brush that may cause damage to the soft and hard tissues of the mouth. A protective sheath envelops the junction between the handle member and the neck member to prevent accumulation of unwanted material within the cavity of the handle.

A second embodiment of the present invention includes all of the components of the first embodiment, but additionally includes a power source and motor to provide vibrational movement to the brush head. Further, the second embodiment includes a manual adjustment that engages the leaf spring at various points along the leaf spring body or incrementally deflects the leaf spring body to provide a variable threshold pressure. Accordingly, a user can adjust the threshold pressure at which the leaf spring gives and moves the neck toward a second position. The neck member is movable between an aligned first position and a second offset position relative to the handle member when a threshold pressure is exceeded. It is additionally contemplated that the handle cavity may be completely or partially filled with a rheostatic fluid or sponge that can affect the degree of flexion of the leaf spring when an electromagnetic force causes the fluid to stiffen by varying degrees.

A third embodiment of the present invention includes all of the components of the first embodiment, but differs insofar as the leaf spring is mounted to the toothbrush handle, and the leaf spring operatively engages the end of the toothbrush neck to provide a biasing force. As with the first embodiment, the leaf spring resistance is such that once a threshold pressure is reached the leaf spring deflects and allows movement of the neck toward a second non-aligned position. The neck member is movable between an aligned first position and a second offset position relative to the handle member when a threshold pressure is exceeded.

A fourth embodiment of the present invention includes all of the components of the third embodiment of the present invention, except that the fourth embodiment includes a power source and a motor for providing vibrational movement to the brush head. Furthermore, the fourth embodiment includes a manual adjustment for engaging the leaf spring at various points along the leaf spring body or incrementally deflects the leaf spring body to aid a user in providing variable threshold pressure. It is additionally contemplated that the handle cavity may be completely or partially filled with a rheostatic fluid or sponge that can affect the degree of flexion of the leaf spring when an electromagnetic force causes the fluid to stiffen by varying degrees.

BRIEF DESCRIPTION OF THE DRAWINGS

Features of the present invention will become more apparent upon reference to the drawings wherein:

FIG. 4 is a cross sectional view of the a first embodiment of the present invention showing the internal components of the invention and movement of the toothbrush neck shown in phantom;

FIG. 5 is a cut away view of a first embodiment of the present invention showing the pivot connection between the handle and neck member of the toothbrush.

FIGS. 6a-6e is a graphical representation of the movement of the neck member in combination with the biasing member at various points of flexion for the first and second embodiments of the present invention;

FIG. 7 is a chart plotting a comparison of flexing angles in relation to pressure of the present invention verses a convention toothbrush;

FIG. 8 is an external view of a second embodiment of the present invention showing internal power components shown in phantom, and a variable pressure adjustment mechanism;

FIG. 9 is an exploded view of a second embodiment of the present invention showing the components of the invention;

FIG. 10 is an exploded view of a second embodiment of the present showing the attachment of the neck portion and the biasing member;

FIG. 11 is a cross sectional view of the a second embodiment of the present invention showing the internal components of the invention and movement of the toothbrush neck shown in phantom;

FIG. 12 is a cut away view of a second embodiment of the present invention showing the pivot connection between the handle and neck member of the toothbrush;

FIGS. 17a-17e is a graphical representation of the movement of the neck member in combination with the biasing member at various points of flexion for the third and fourth embodiments of the present invention;

DETAILED DESCRIPTION OF THE INVENTION

Figure 1:
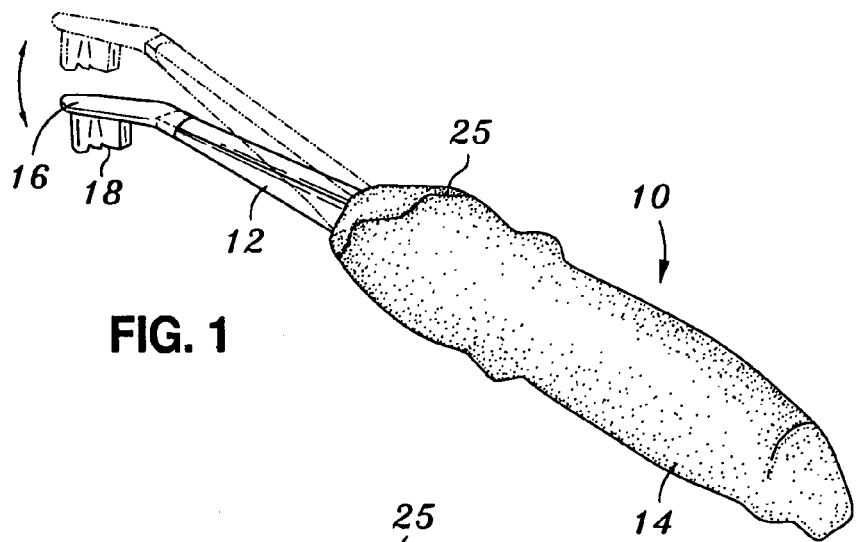
FIG. 1 is an external view of a first embodiment of the present invention showing movement of the toothbrush neck.
Figure 2:
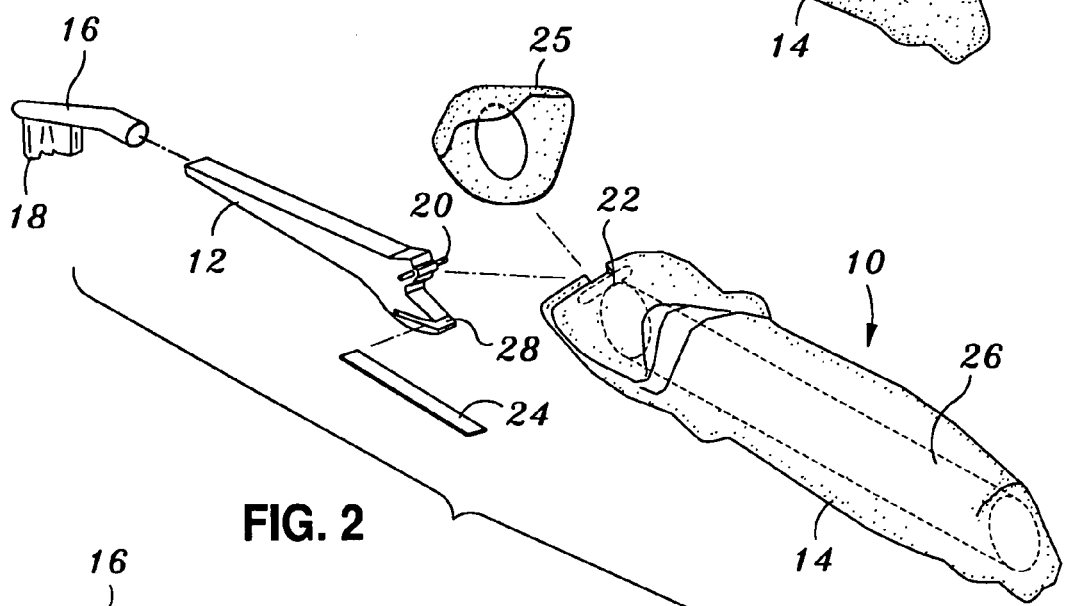
FIG. 2 is an exploded view of a first embodiment of the present invention showing the components of the invention.
Figure 3:
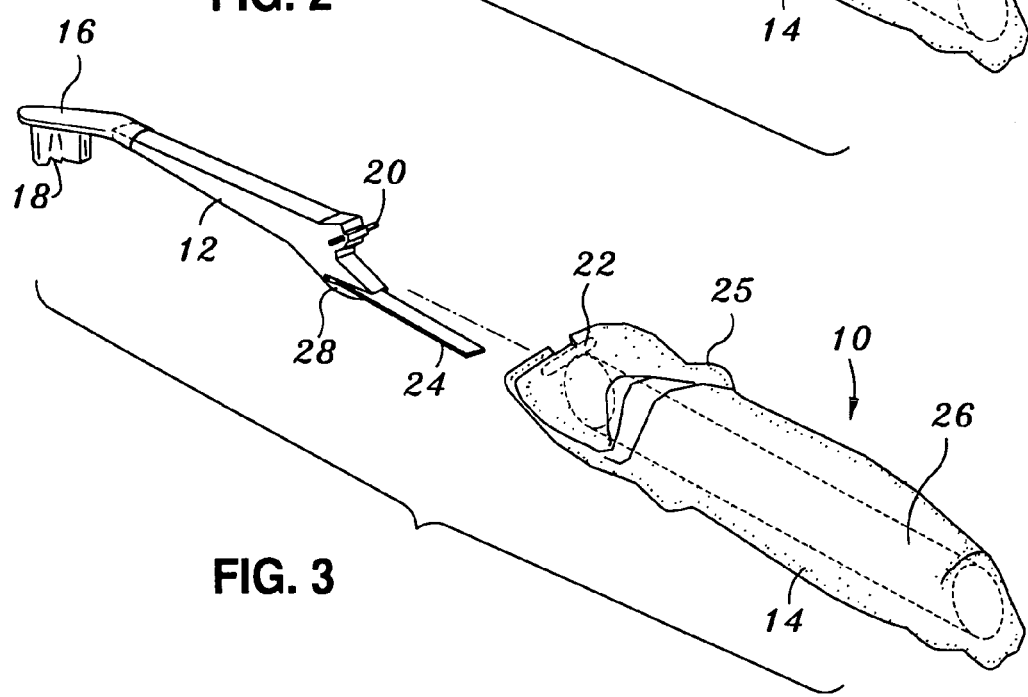
FIG. 3 is an exploded view of a first embodiment of the present showing the attachment of the neck portion and the biasing member.
Figure 13:
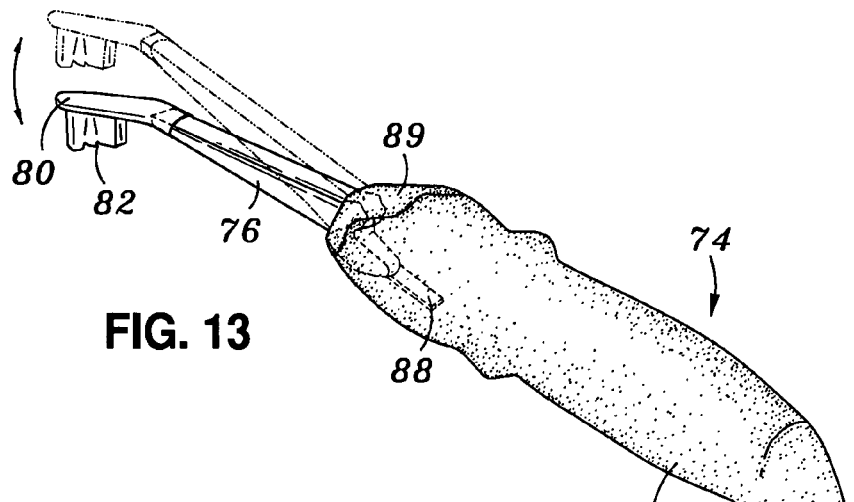
FIG. 13 is an external view of a third embodiment of the present invention showing movement of the toothbrush neck.
Figure 14:
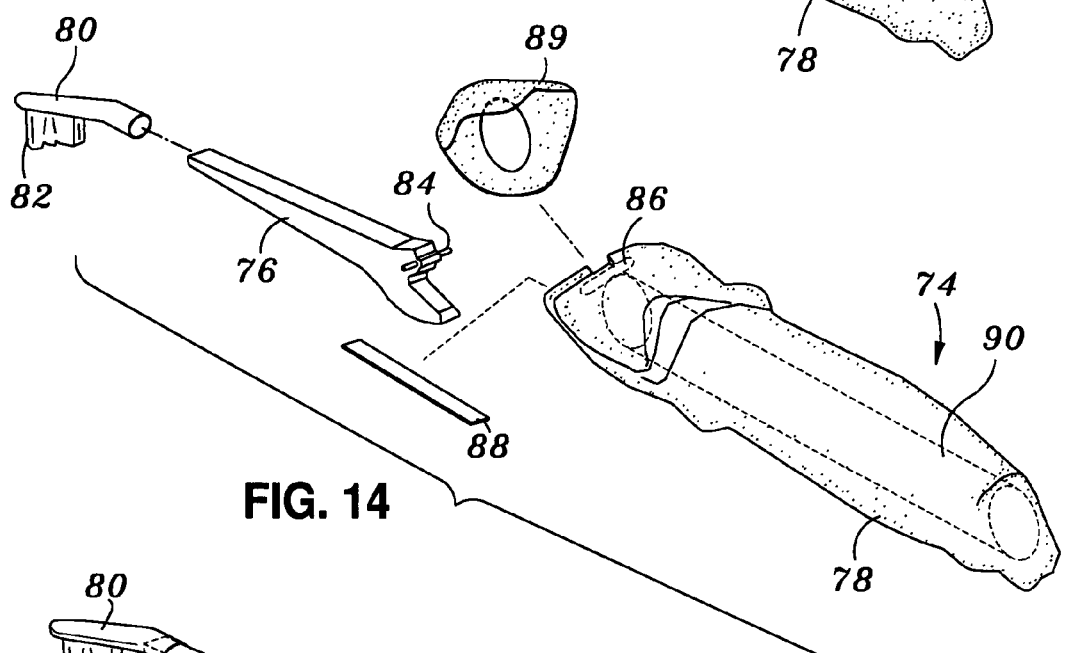
FIG. 14 is an exploded view of a third embodiment of the present invention showing the components of the invention.
Figure 15:
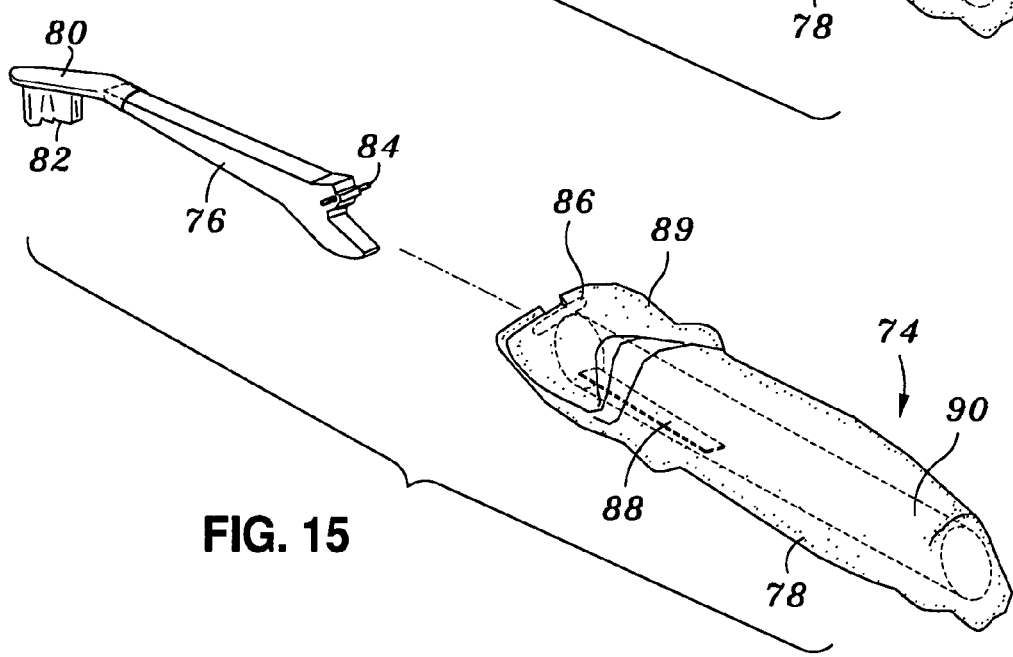
FIG. 15 is an exploded view of a third embodiment of the present showing the attachment of the handle portion and the biasing member.

The detailed description as set forth below in connection with the appended drawings is intended as a description of the presently preferred embodiments of the present invention, and does not represent the only embodiment of the present invention. It is understood that various modifications to the invention may be comprised by different embodiments and are also encompassed within the spirit and scope of the present invention.

Referring to the drawings, wherein like reference numerals refer to the same or similar elements among FIGS. 1 through 5, there is shown a toothbrush 10 in accordance with a first embodiment of the present invention. Toothbrush 10 contains a neck member 12 and a handle member 14. Toothbrush 10 additionally includes a head section 16 having brush bristles 18. The head 16 is connected to the neck member 12 by a frictional fit as best illustrated in FIG. 4 wherein the neck member 12 is inserted within an aperture (not shown) of the head member 16. The head member 16 may be secured by an inert epoxy or otherwise fixed to the neck member 12. It is contemplated in this embodiment, as well as all embodiments as set forth herein, that the connection between the neck member 12 and the head member 16 may additionally include an elastomer coupler. The elastomer coupler may be provided as a movable joint that provides additional flexibility in the head member 16 relative to the neck member 12.

The handle member 14, the neck member 12 and the head member 16 are preferably molded of a relatively rigid plastic such as polypropylene or polyethylene terephthalate or other suitable polyester. Conventional uses of polypropylene and polyester molded plastics used in toothbrush configurations may be found in U.S. Pat. No. 6,502,272, the substance of which is incorporated herein by reference. In addition, any elastomer couplers utilized in any of the embodiments of the present invention can be molded of thermal plastic elastomer or combination thereof, including a thermal plastic vulcanite (TPV). Brand names of such TPV material is Santoprene (brand), Vyram (brand) as commercially available from Advanced Elastomer Systems LP, Akron, Ohio. Another preferred elastomer is Dynaflex G6713 (brand) a thermal plastic elastomer marketed by GLS Corp. of Cary, Ill. Such elastomers are described in more detail in U.S. Pat. No. 6,502,272, the substance of which is incorporated herein by reference.

The neck member 12 is pivotally connected to the handle member by a pivot mechanism comprising the combination of a male component in the form of a pivot bar 20 formed on the proximal end of the neck member 12 and a pivot slot 22 formed in the distal end of the handle member 14. The pivot mechanism 20, 22 forms the junction between the neck member 12 and handle member 14. Pivot bar 20 extends through the neck member 12 and interfaces with the distal end of the handle member 14 as pivot slot 22. The pivot bar 20 is received within the pivot slot 22 to allow pivotal movement of the neck member 12 relative the handle member 14. A cavity 26 is formed in the handle member 14.

A leaf spring 24 is embedded into the proximal end of the neck member 12. The leaf spring 24 is inserted into the handle cavity 26 when the pivot bar 20 engages the pivot slot 22. The leaf spring 24 engages the interior surface of the cavity 26 to provide a biasing force when pressure is applied to the toothbrush head 16. Protective sheath 25 envelops the junction between the distal end of the handle member 14 and the proximal end of the neck member 12. Leaf spring 24 for purposes of this first embodiment, as well as each embodiment described herein is comprised of a high-grade plastic having appropriate spring-like characteristics. In this regard, it may be formed in each of the embodiments from a fiber-reinforced plastic, wherein such fibers may be made of glass or carbon fibers. The leaf spring 24 can be separately injected molded and then inserted or injection mold integrated into the neck member 12. It is additionally contemplated by all embodiments of the present invention that the leaf spring 24 while shown as being flat can have a polygonal, round, oval, U, T, or I cross-section. Also, it is contemplated that the leaf spring 24 may be formed as a metallic leaf spring that is either injected molded into the plastic of the neck member 12 or otherwise embedded within a preformed slot 28 in the proximal end of the neck member 12. In this regard, the leaf spring 24 is configured with materials and dimensions such that it holds the neck member 12 and handle member 14 in substantial alignment when no pressure is applied or when a pressure is applied that is less than the threshold pressure. When a force is applied to the head of the brush 16 that exceeds a threshold pressure, the leaf spring 24 deflects and allows movement of the neck member 12 toward an offset position. The neck member 12 is movable between an aligned first position and a second offset position relative to the handle member 14 when a threshold pressure is exceeded. The threshold pressure is the pressure upon the brush head 16 just before the pressure level that may cause damage to the hard and soft tissues of the mouth. Once deflected, the neck cannot impart increasing pressure upon the dental structures, and with ever-increasing handle force, the angle of displacement may become great enough to discourage the user from continuing to brush with the toothbrush 10 in the furthest deflected state. Once the pressure is released to zero or reduced to below the threshold level the leaf spring 24 immediately begins resetting toward the original aligned position. The angle of displacement only becomes discouraging to the user if far too much force is applied. Once threshold pressure is exceeded, the neck moves unimpeded out of alignment. This unimpeded movement allows users with limited time, poor dexterity, or low cognition to brush improperly without causing damage to the oral tissues. The unimpeded movement once the threshold pressure is exceeded also allows the neck to quickly and easily displace and reset around obstacles, irregularities and curvatures of the mouth, thus avoiding unwanted oral trauma.

Referring particularly to FIG. 4, there is shown a cross-sectional view of the first embodiment of the present invention. The leaf spring 24 engages the interior surface 30 of the cavity 26 in the handle member 14. The toothbrush is shown with the neck in a first position, and toothbrush 10 will remain in this position so long as a safe threshold pressure is applied at the toothbrush head 16. When the safe threshold pressure is exceeded, the leaf spring deflects as shown in the phantom leaf spring 32 and the phantom neck member 34 toward a second offset position at the exceeded threshold pressure. In the embodiments of the present invention, the neck 12 does not immediately move or snap out to a second position after a threshold pressure is exceeded. During use, after the threshold pressure is reached, no increasing pressure can be applied to the oral tissue, and any attempt to increase pressure by the user results in unimpeded movement of the neck 12 as it rotates about the pivot mechanism 20, 22 toward the maximum rotation point. Because of the elastic nature of the leaf spring 24 and the arrangement of the leaf spring 24 in cooperation with the neck 12 and handle 14 members, the brush 10 always instantaneously attempts to reset toward the aligned position as soon as the pressure is reduced. Unlike brushes with elastomeric flexibility features, the toothbrush 10 of the present invention does not suffer from temporary extended deformation before resetting. Thus, the brush 10 adapts to the curvature of the dental arch even during normal brushing, and immediately resets toward a normal position.

Referring particularly to FIGS. 6a through 6e, there is shown a graphical representation of the toothbrush 10 device of the first embodiment of the present invention. FIG. 6a shows the neck member 12 in combination with the leaf spring 24 in a normal position when no pressure is being applied. FIG. 6b represents the toothbrush when a safe pressure is being applied, and the neck 12 and leaf spring 24 remain in a first position. When the safe pressure is exceeded, the leaf spring 24 deflects allowing movement of the neck member 12 as shown in FIGS. 6c-6e in varying degrees. FIGS. 6d and 6e represent the toothbrush wherein the leaf spring 24 has deflected to its maximum amount limited by the pivot bar 20 and pivot slot 22 as shown more particularly in FIG. 5.

Referring particularly to FIG. 7, a chart is shown representing a comparison of flexing angles versus pressures on the brush head of the various embodiments of the present invention. The present invention is shown in comparison with a standard flexible neck toothbrush. As is evident from the graph, pressure on the standard flexible neck brush continues to increase well beyond the safe threshold level. The device of the present invention maintains the pressure level at the brush well below the safe threshold level.

Referring to the drawings, namely FIGS. 8 through 11, wherein like reference numerals refer to the same or similar elements among the figures, there is shown a toothbrush 36 in accordance with a second embodiment of the present invention. The second embodiment of the present invention is distinguished from the first embodiment of the present invention primarily by the inclusion of power components that allow the toothbrush to operate as an electric toothbrush. In addition, a manual pressure adjustment is provided to provide a variable threshold pressure. Toothbrush 36 contains a neck member 38 and a handle member 40. Toothbrush 36 additionally includes a head section 42 having brush bristles 44. The head 42 is connected to the neck member 38 by a frictional fit as best illustrated in FIG. 11 wherein the neck member 38 is inserted within an aperture (not shown) of the head member 42. The head member 42 may be secured by an inert epoxy or otherwise fixed to the neck member 38. It is contemplated in this embodiment, as well as all embodiments as set forth herein, that the connection between the neck member 38 and the head member 42 may additionally include an elastomer coupler. The elastomer coupler may be provided as a movable joint that provides additional flexibility in the head member 42 relative to the neck member 38. The handle member 40, the neck member 38 and the head member 42 are preferably molded of a relatively rigid plastic such as polypropylene or polyethylene terephthalate or other suitable polyester.

The neck member 38 is pivotally connected to the handle member by a pivot mechanism comprising the combination of a male component in the form of a pivot bar 46 formed on the proximal end of the neck member 38 and a pivot slot 48 formed in the distal end of the handle member 40. The pivot mechanism 46, 48 forms the junction between the neck member 38 and handle member 40. Pivot bar 46 extends through the neck member 38 and interfaces with the distal end of the handle member 40 as pivot slot 48. The pivot bar 46 is received within the pivot slot 48 to allow pivotal movement of the neck member 38 relative the handle member 40. A cavity 52 is formed in the handle member 40.

A leaf spring 50 is embedded into the proximal end of the neck member 38. The leaf spring 50 is inserted into the handle cavity 54 when the pivot bar 46 engages the pivot slot 48. The leaf spring 50 engages the interior surface of the cavity 52 to provide a biasing force when pressure is applied to the toothbrush head 42. Protective sheath 51 envelops the junction between the distal end of the handle member 40 and the proximal end of the neck member 38. Leaf spring 50 for purposes of this second embodiment, as well as each embodiment described herein is comprised of a high-grade plastic having appropriate spring-like characteristics. In this regard, it may be formed in each of the embodiments from a fiber-reinforced plastic, wherein such fibers may be made of glass or carbon fibers. The leaf spring 50 can be separately injected molded and then inserted or injection mold integrated into the neck member 38. It is additionally contemplated by all embodiments of the present invention that the leaf spring 50 while shown as being flat can have a polygonal, round, oval, U, T, or I cross-section. Also, it is contemplated that the leaf spring 50 may be formed as a metallic leaf spring that is either injected molded into the plastic of the neck member 38 or otherwise embedded within a preformed slot 54 in the proximal end of the neck member 38. In this regard, the leaf spring 50 is configured with materials and dimensions such that it holds the neck member 38 and handle member 40 in substantial alignment when no pressure is applied or when a pressure is applied that is less than the threshold pressure. When a force is applied to the head of the brush 42 that exceeds a selected threshold pressure, the leaf spring 50 deflects and allows movement of the neck member 38 toward an offset position. The neck member 38 is movable between an aligned first position and a second offset position relative to the handle member 40 when a threshold pressure is exceeded. The threshold pressure in this embodiment is a variable that can be set anywhere from just barely above the force required to overcome spring tension and friction to a pressure upon the brush head 42 just before the pressure level that may cause damage to the hard and soft tissues of the mouth. Once deflected, the neck cannot impart increasing pressure upon the dental structures, and with ever-increasing handle force, the angle of displacement can become great enough to discourage the user from continuing to brush with the toothbrush 36 in the furthest deflected state. Once the pressure is released to zero or reduced to below the threshold level the leaf spring 50 immediately attempts resetting to the original aligned position. The angle of displacement only becomes discouraging to the user if far too much force is applied. Once threshold pressure is exceeded, the neck moves unimpeded out of alignment. This unimpeded movement allows users with limited time, poor dexterity, or low cognition to brush improperly without causing damage to the oral tissues. The unimpeded movement once the threshold pressure is exceeded also allows the neck to quickly and easily displace and reset around obstacles, irregularities and curvatures of the mouth, thus avoiding unwanted oral trauma.

Batteries 68 located in the handle member 40 cavity 52 provide power to a motor 67. The motor 67 provides vibrational movement to the head 42 through a flexible connector 70. Buttons 72 provide manual control of the motor 67.

The manual adjustment of the threshold pressure of the leaf spring 50 is effected through a manual adjustment knob 62. Rotational movement of the knob 62 translates to rotational movement of a shaft 64 deep within the device 36 structure. A helical structure 66 affixed to the end of the shaft 64 engages the leaf spring 50 to provide variable resistance against the leaf spring 50, thus modifying the pressure level of the leaf spring 50 deflection. Alternatively, the helical structure 66 could be a coil, polygonal structure or cam structure configured to lift and lower the deflection point. Accordingly, a user can "dial" in a desired pressure for use with the brush 36. Currently, after mouth surgery or other injury to the mouth, a doctor may recommend use of an ultra soft bristle brush with low brushing pressure, and to graduate to stiffer bristles and increased brushing pressure as the mouth heals. The adjustable nature of the toothbrush 36 of the present invention allows a person to use a single brush to accomplish varying degrees of brushing pressure.

Referring particularly to FIG. 11, there is shown a cross-sectional view of the second embodiment of the present invention. The leaf spring 50 engages the interior surface 56 of the cavity 52 in the handle member 40. The toothbrush is shown with the neck in a first position, and toothbrush 36 will remain in this position so long as a selected threshold pressure is applied at the toothbrush head 42. When the selected threshold pressure is exceeded, the leaf spring deflects as shown in the phantom leaf spring 58 and the phantom neck member 60 toward a second offset position at the exceeded threshold pressure. In the embodiments of the present invention the neck 38 does not immediately move or snap out to a second position after a threshold pressure is exceeded; in operation, after the threshold pressure is reached, no increasing pressure can be applied to the oral tissues, and any attempt to increase pressure by the user results in unimpeded movement of the neck 38 as it rotates about the pivot mechanism 46, 48 toward the maximum rotation point. Because of the elastic nature of the leaf spring 50 and the arrangement of the leaf spring 50 in cooperation with the neck 38 and handle 40 members, the brush 36 instantaneously attempts to reset toward the aligned position as soon as the pressure is reduced. Unlike brushes with elastomeric flexibility features, the toothbrush 10 of the present invention does not suffer from temporary extended deformation before resetting. Thus the brush 10 adapts to the curvature of the dental arch even during normal brushing, and always immediately attempts resetting toward a normal position.

Figure 16:
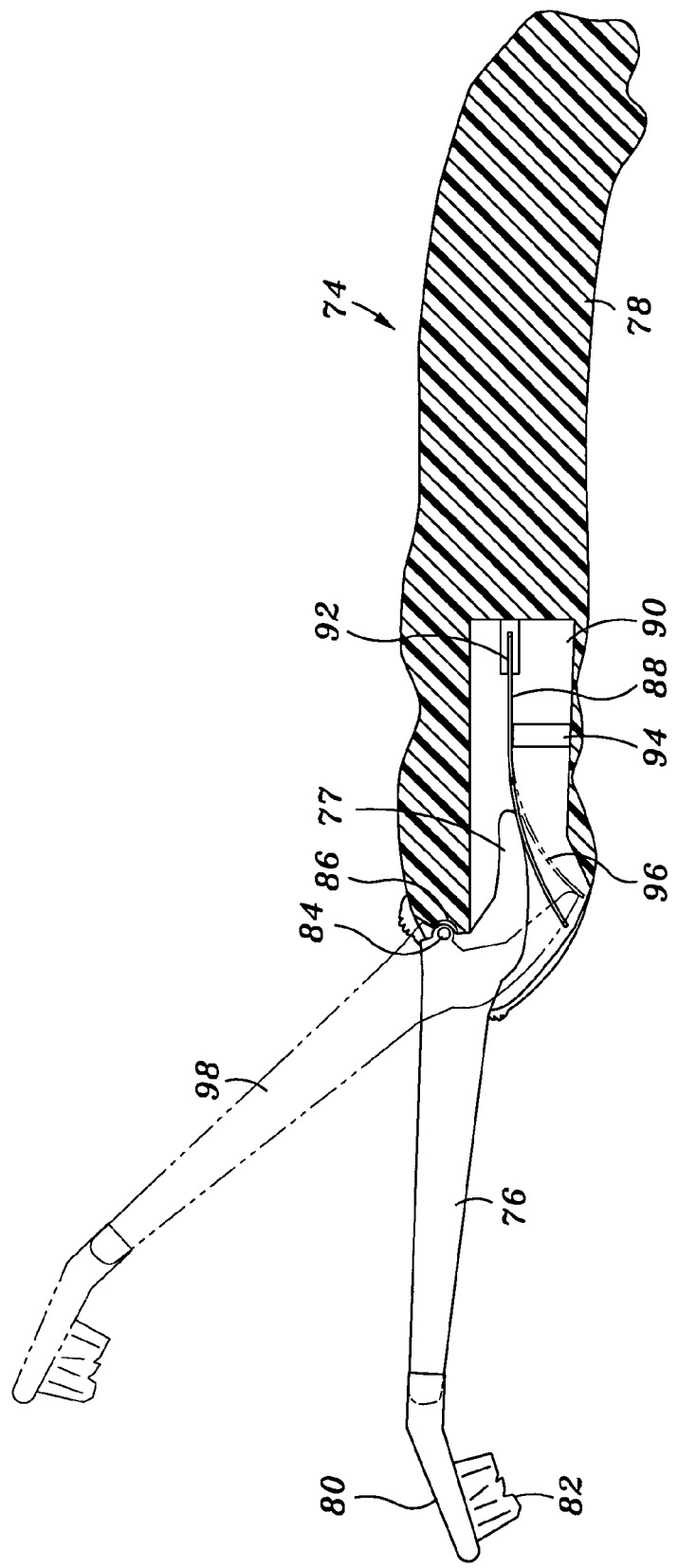
FIG. 16 is a cross sectional view of the a third embodiment of the present invention showing the internal components of the invention and movement of the toothbrush neck shown in phantom.
Figure 18:
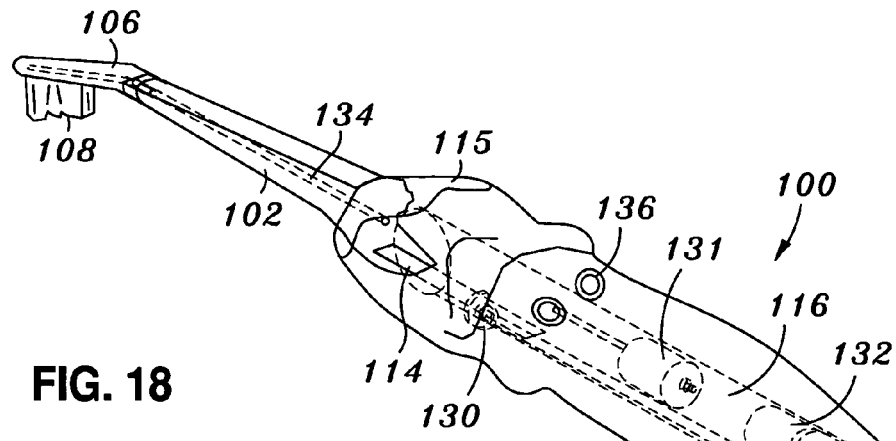
FIG. 18 is an external view of a fourth embodiment of the present invention showing internal power components shown in phantom, and a variable pressure adjustment mechanism.
Figure 19:
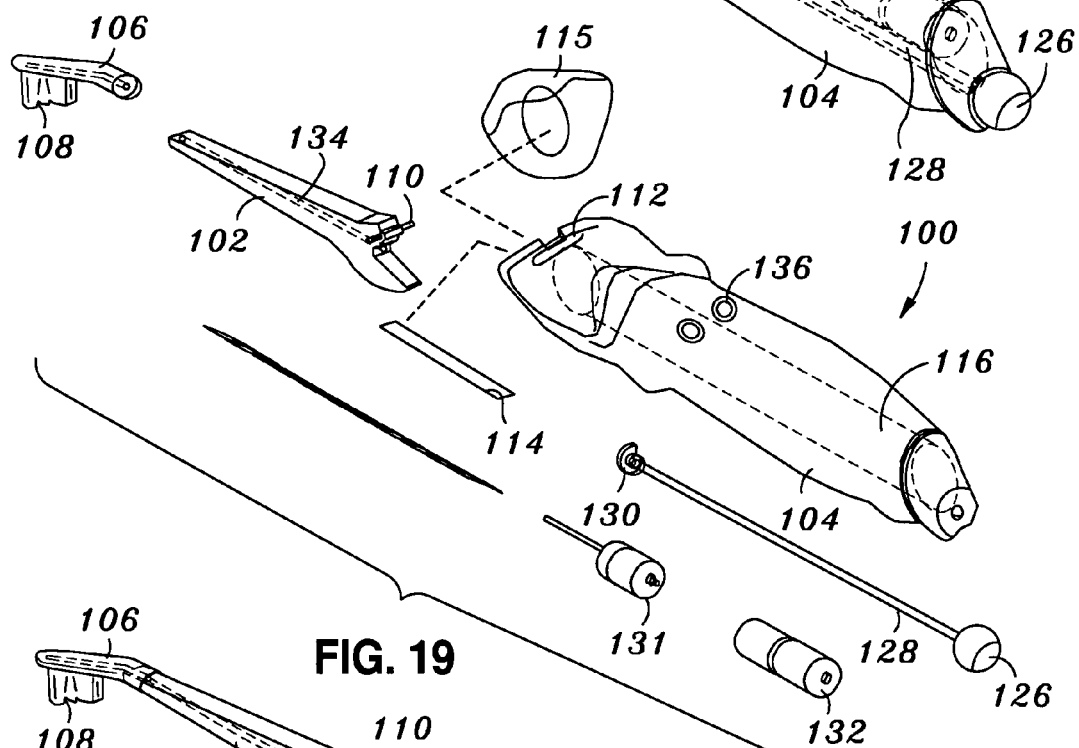
FIG. 19 is an exploded view of a fourth embodiment of the present invention showing the components of the invention.
Figure 20:
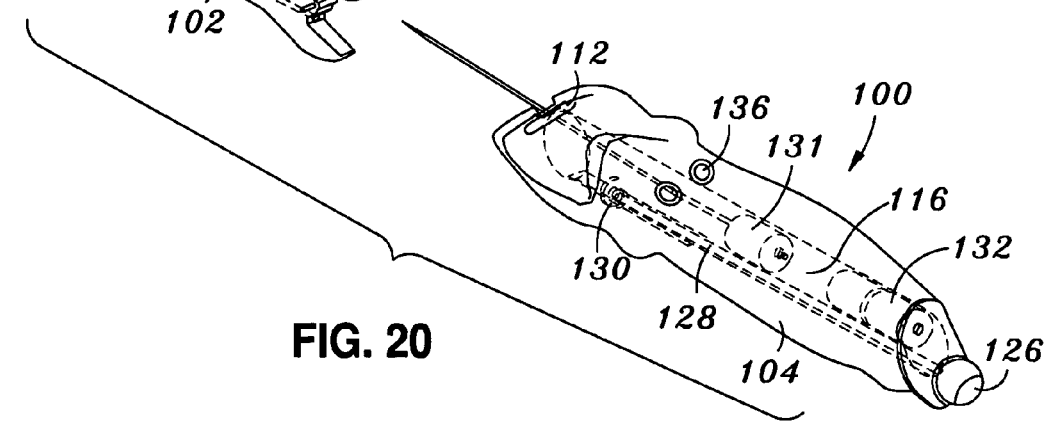
FIG. 20 is an exploded view of a fourth embodiment of the present showing the attachment of the handle portion and the biasing member.

Referring to FIGS. 13 through 16, wherein like reference numerals refer to the same or similar elements among the drawings, there is shown a toothbrush 74 in accordance with a third embodiment of the present invention. The third embodiment of the present invention is distinguished from the first embodiment of the present invention primarily by the affixation of the leaf spring 88 to the handle member 78 rather than the neck member 76. Toothbrush 74 contains a neck member 76 and a handle member 78. Toothbrush 74 additionally includes a head section 80 having brush bristles 82. The head 80 is connected to the neck member 76 by a frictional fit as best illustrated in FIG. 16 wherein the neck member 76 is inserted within an aperture (not shown) of the head member 80. The head member 80 may be secured by an inert epoxy or otherwise fixed to the neck member 76. It is contemplated in this embodiment, as well as all embodiments as set forth herein, that the connection between the neck member 76 and the head member 80 may additionally include an elastomer coupler. The elastomer coupler may be provided as a movable joint that provides additional flexibility in the head member 80 relative to the neck member 76. The handle member 78, the neck member 76 and the head member 80 are preferably molded of a relatively rigid plastic such as polypropylene or polyethylene terephthalate or other suitable polyester.

The neck member 76 is pivotally connected to the handle member by a pivot mechanism comprising the combination of a male component in the form of a pivot bar 84 formed on the proximal end of the neck member 76 and a pivot slot 86 formed in the distal end of the handle member 78. The pivot mechanism 84, 86 forms the junction between the neck member 76 and handle member 78. Pivot bar 84 extends through the neck member 76 and interfaces with the distal end of the handle member 78 as pivot slot 86. The pivot bar 84 is received within the pivot slot 86 to allow pivotal movement of the neck member 76 relative the handle member 78. A cavity 26 is formed in the handle member 78.

A leaf spring 88 is embedded into the distal end of the handle member 78. The leaf spring 88 engages the proximal end of the neck member 76 when the pivot bar 84 engages the pivot slot 86. The leaf spring 88 engages the surface the proximal end of he neck member 76 to provide a biasing force when pressure is applied to the toothbrush head 80. Protective sheath 89 envelops the junction between the distal end of the handle member 78 and the proximal end of the neck member 76. Leaf spring 88 for purposes of this third embodiment, as well as each embodiment described herein is comprised of a high-grade plastic having appropriate spring-like characteristics. In this regard, it may be formed in each of the embodiments from a fiber-reinforced plastic, wherein such fibers may be made of glass or carbon fibers. The leaf spring 88 can be separately injected molded and then inserted or injection mold integrated into the handle member 78. It is additionally contemplated by all embodiments of the present invention that the leaf spring 88 while shown as being flat can have a polygonal, round, oval, U, T, or I cross-section. Also, it is contemplated that the leaf spring 88 may be formed as a metallic leaf spring which is either injected molded into the plastic of the handle member 78 or otherwise embedded within a preformed slot 92 formed in the cavity 90 of the handle member 78 as best shown in FIG. 16. In this regard, the leaf springs 88 is configured with materials and dimension such that it holds the neck member 76 and handle member 78 in substantial alignment when no pressure is applied or when a pressure is applied that is less than a threshold pressure. When a force is applied to the head of the brush 80 that exceeds the threshold pressure, the leaf spring 88 deflects and allows movement of the neck member 76 toward an offset position. The neck member 76 is movable between an aligned first position and a second offset position relative to the handle member 78 when a threshold pressure is exceeded. The threshold pressure is the pressure upon the brush head 80 just before the pressure level that may cause damage to the hard and soft tissue of the mouth. Once deflected, the neck cannot impart increasing pressure upon the dental structures, and with ever-increasing handle force, the angle of displacement may become great enough to discourage the user from continuing to brush with the toothbrush 74 in the furthest deflected state. Once the pressure is released to zero or reduced to below the threshold level the leaf spring 88 attempts resetting toward the original aligned position. The angle of displacement only becomes discouraging to the user if far too much force is applied. Once threshold pressure is exceeded, the neck moves unimpeded out of alignment. This unimpeded movement allows users with limited time, poor dexterity, or low cognition to brush improperly without causing damage to the oral tissues. The unimpeded movement once the threshold pressure is exceeded also allows the neck to quickly and easily displace and reset around obstacles, irregularities and curvatures of the mouth, thus avoiding unwanted oral trauma.

Referring particularly to FIG. 16, there is shown a cross-sectional view of the third embodiment of the present invention. The leaf spring 88 engages the proximal end of the neck member 76. The neck member 76 has a curved flange 77 for engaging the leaf spring 88. The toothbrush is shown with the neck in a first position, and toothbrush 74 will remain in this position so long as a safe pressure is applied at the toothbrush head 80. When the safe pressure is exceeded, the leaf spring deflects as shown in the phantom leaf spring 96 and the phantom neck member 98 toward a second offset position at the exceeded threshold pressure. In the embodiments of the present invention the neck 76 does not immediately move or snap out to a second position after a threshold pressure is exceeded; in operation, after the threshold pressure is reached, no increasing pressure can be applied to the oral tissue, and any attempt to increase pressure by the user results in unimpeded movement of the neck 76 as it rotates about the pivot mechanism 84, 86 toward the maximum rotation point. Because of the elastic nature of the leaf spring 88 and the arrangement of the leaf spring 88 in cooperation with the neck 76 and handle 78 members, the brush 74 always instantaneously attempts resetting toward the aligned position as soon as the pressure is reduced. Unlike brushes with elastomeric flexibility features, the toothbrush 74 of the present invention does not suffer from temporary extended deformation before resetting. Thus, the brush 74 adapts to the curvature of the dental arch even during normal brushing, and immediately resets toward a normal position.

Referring particularly to FIGS. 17a through 17e, there is shown a graphical representation of the toothbrush 74 device of the third embodiment of the present invention. FIG. 17a shows the neck member 76 in combination with the leaf spring 88 in a normal position when no pressure is being applied. FIG. 17b represents the toothbrush when a safe pressure is being applied, and the neck 76 and leaf spring 88 remain in a first position. When the safe pressure is exceeded, the leaf spring 88 deflects allowing movement of the neck member 76 as shown in FIGS. 17c-17e in varying degrees. FIGS. 17d and 17e represent the toothbrush wherein the leaf spring 88 has deflected to its maximum amount limited by the pivot bar 84 and pivot slot 86.

Figure 21:
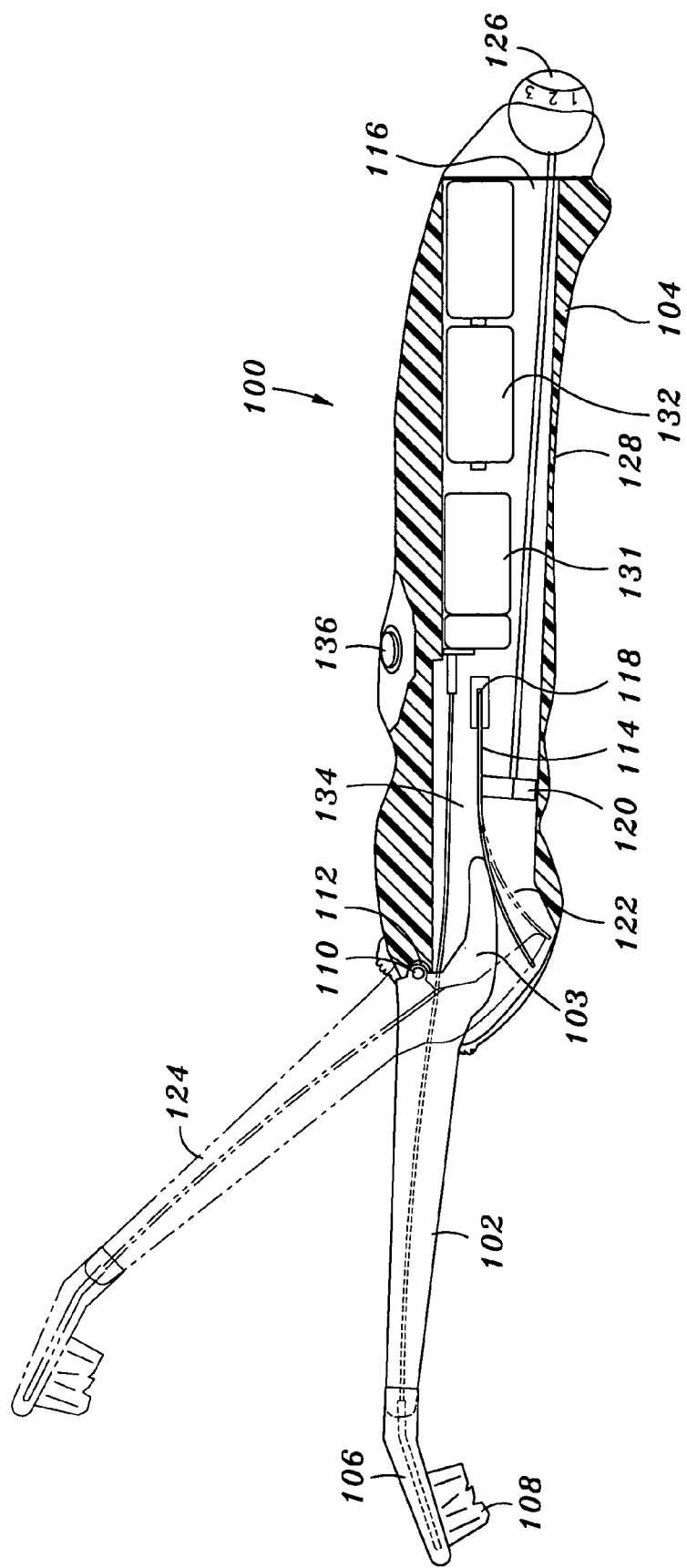
FIG. 21 is a cross sectional view of the fourth embodiment of the present invention showing the internal components of the invention and movement of the toothbrush neck shown in phantom.

Referring to the drawings, namely FIGS. 18 through 21, wherein like reference numerals refer to the same or similar elements among the figures, there is shown a toothbrush 100 in accordance with a fourth embodiment of the present invention. The fourth embodiment of the present invention is distinguished from the third embodiment of the present invention primarily by the inclusion of power components that allow the toothbrush to operate as an electric toothbrush. In addition, a manual pressure adjustment is provided to provide a variable threshold pressure. Toothbrush 100 contains a neck member 102 and a handle member 104. Toothbrush 100 additionally includes a head section 106 having brush bristles 108. The head 106 is connected to the neck member 102 by a frictional fit as best illustrated in FIG. 21 wherein the neck member 102 is inserted within an aperture (not shown) of the head member 106. The head member 106 may be secured by an inert epoxy or otherwise fixed to the neck member 102. It is contemplated in this embodiment, as well as all embodiments as set forth herein, that the connection between the neck member 102 and the head member 106 may additionally include an elastomer coupler. The elastomer coupler may be provided as a movable joint that provides additional flexibility in the head member 106 relative to the neck member 102. The handle member 104, the neck member 102 and the head member 106 are preferably molded of a relatively rigid plastic such as polypropylene or polyethylene terephthalate or other suitable polyester.

The neck member 102 is pivotally connected to the handle member by a pivot mechanism comprising the combination of a male component in the form of a pivot bar 110 formed on the proximal end of the neck member 102 and a pivot slot 112 formed in the distal end of the handle member 104. The pivot mechanism 110,112 forms the junction between the neck member 102 and handle member 104. Pivot bar 110 extends through the neck member 102 and interfaces with the distal end of the handle member 104 as pivot slot 112. The pivot bar 110 is received within the pivot slot 112 to allow pivotal movement of the neck member 102 relative the handle member 104. A cavity 116 is formed in the handle member 104.

A leaf spring 114 is embedded into the distal end of the handle member 104. The leaf spring 114 engages the proximal end of the neck member 102 when the pivot bar 110 engages the pivot slot 112. The leaf spring 114 engages the surface the proximal end of he neck member 102 to provide a biasing force when pressure is applied to the toothbrush head 106. Protective sheath 115 envelops the junction between the distal end of the handle member 104 and the proximal end of the neck member 102. Leaf spring 114 for purposes of this fourth embodiment, as well as each embodiment described herein is comprised of a high-grade plastic having appropriate spring-like characteristics. In this regard, it may be formed in each of the embodiments from a fiber-reinforced plastic, wherein such fibers may be made of glass or carbon fibers. The leaf spring 114 can be separately injected molded and then inserted or injection mold integrated into the handle member 104. It is additionally contemplated by all embodiments of the present invention that the leaf spring 114 while shown as being flat can have a polygonal, round, oval, U, T, or I cross-section. Also, it is contemplated that the leaf spring 114 may be formed as a metallic leaf spring that is either injected molded into the plastic of the handle member 104 or otherwise embedded within a preformed slot 118 formed in the cavity 116 of the handle member 104 as best shown in FIG. 21. In this regard, the leaf spring 114 is configured with materials and dimensions such that it holds the neck member 102 and handle member 104 in substantial alignment when no pressure is applied or when a pressure is applied that is less than the threshold pressure. When a force is applied to the head of the brush 106 that exceeds a selected threshold pressure, the leaf spring 114 deflects and allows movement of the neck member 102 toward an offset position. The neck member 102 is movable between an aligned first position and a second offset position relative to the handle member 104 when a threshold pressure is exceeded. The threshold pressure in this embodiment is a variable that can be set anywhere form just barely above the force required to overcome spring tension and friction, to a pressure upon the brush head 106 just before the pressure level that may cause damage to the hard and soft tissues of the mouth. Once deflected, the neck cannot impart increasing pressure upon the dental structures, and with ever-increasing handle force, the angle of displacement can become great enough to discourage the user from continuing to brush with the toothbrush 100 in the furthest deflected state. Once the pressure is released to zero or reduced to below the threshold level the leaf spring 114 immediately attempts resetting toward the original aligned position. The angle of displacement only becomes discouraging to the user if far too much force is applied. Once threshold pressure is exceeded, the neck moves unimpeded out of alignment. This unimpeded movement allows users with limited time, poor dexterity, or low cognition to brush improperly without causing damage to the oral tissues. The unimpeded movement once the threshold pressure is exceeded also allows the neck to quickly and easily displace and reset around obstacles, irregularities and curvatures of the mouth, thus avoiding unwanted oral trauma.

Batteries 132 located in the handle member 104 cavity 116 provide power to a motor 131. The motor 131 provides vibrational movement to the head 106 through a flexible connector 134. Buttons 136 provide manual control of the motor 131.

The manual adjustment of the threshold pressure of the leaf spring 114 is effected through a manual adjustment knob 126. Rotational movement of the knob 126 translates to rotational movement of a shaft 128 deep within the device 100 structure. A helical structure 130 affixed to the end of the shaft 128 engages the leaf spring 114 to provide variable resistance against the leaf spring 114, thus modifying the pressure level of the leaf spring 114 deflection. Alternatively, the helical structure 130 could be a coil, polygonal structure or cam structure configured to lift and lower the deflection point. Accordingly, a user can "dial" in a desired pressure for use with the brush 100. Currently, after mouth surgery or other injury to the mouth, a doctor may recommend use of an ultra soft bristle brush and/or light brushing pressure, and to graduate to stiffer bristles and/or more pressure as the mouth heals. The adjustable nature of the toothbrush 100 of the present invention allows a person to use a single brush to accomplish varying degrees of stiffness.

Referring particularly to FIG. 21, there is shown a cross-sectional view of the fourth embodiment of the present invention. The leaf spring 114 engages the proximal end of the neck member 102. The neck member 102 has a curved flange 103 for engaging the leaf spring 114. The toothbrush is shown with the neck in a first position, and toothbrush 100 will remain in this position so long as a selected threshold pressure is applied at the toothbrush head 106. When the selected threshold pressure is exceeded, the leaf spring deflects as shown in the phantom leaf spring 122 and the phantom neck member 124 toward a second offset position at the exceeded threshold pressure. In the embodiments of the present invention the neck 102 does not immediately move or snap out to a second position after a threshold pressure is exceeded; in operation, after the threshold pressure is reached, no increasing pressure can be applied to the oral tissue, and any attempt to increase pressure by the user results in unimpeded movement of the neck 102 as it rotates about the pivot mechanism 110, 112 toward the maximum rotation point. Because of the elastic nature of the leaf spring 114 and the arrangement of the leaf spring 114 in cooperation with the neck 102 and handle 104 members, the brush 100 instantaneously attempts resetting toward the aligned position as soon as the pressure is reduced. Unlike brushes with elastomeric flexibility features, the toothbrush 100 of the present invention does not suffer from temporary extended deformation before resetting. Thus, the brush 100 adapts to the curvature of the dental arch even during normal brushing, and immediately tries to reset toward a normal position.

Additional modifications to the method of the present invention and the devices used in accordance with the method will be apparent to those skilled in the art. It is understood that such additional modifications are within the scope and spirit of the present invention.

What is claimed is:

1. An ergonomic toothbrush having a flexible neck and adaptively designed handle to prevent tooth abrasion and gum damage comprising:
  a. a handle member defining a distal end and a proximal end, said distal end including an open cavity defining an interior surface;
  b. a neck member defining a distal end and a proximal end, said distal end including a dental brush and said proximal end pivotally connected to the distal end of the handle member and said neck member movable between a first position wherein the handle member and neck member are substantially aligned and a second position angularly offset relative to the handle;
  c. a leaf spring defining a first end, second end and spring body; said first end bonded to said neck member, wherein movement of the neck member about the pivotal connection translates movement of the spring body within the cavity of the handle member; said spring body adapted to engage the interior surface to provide biasing resistance;
  wherein said leaf spring is operative to normally bias the neck member to the first position and is configured such that the application of pressure to the neck portion beyond a prescribed threshold facilitates movement of the neck portion from the first position to the second position.

2. The flexible neck toothbrush of claim 1 wherein said neck member is angularly offset relative to the handle member at an angle in the range from 1 degree to 45 degrees when in the second position.

3. The flexible neck toothbrush of claim 1 wherein said prescribed threshold pressure is the pressure upon the dental brush that causes deflection of the biasing member.

4. The flexible neck toothbrush of claim 1 further comprising an adjustable member for engaging the leaf spring at various points along the length of the spring body to provide the variable threshold pressure.

5. The flexible neck toothbrush of claim 1 wherein said cavity is at least partially filled with a rheostatic fluid.

6. The flexible neck toothbrush of claim 1 wherein said cavity incorporates a rheostatic sponge.

7. An ergonomic toothbrush having a flexible neck and adaptively designed handle to prevent tooth abrasion and gum damage comprising:
   a. a handle member incorporating a dental brush;
   b. a neck member pivotally connected handle member, said neck member movable between a first position wherein the handle member and neck member are substantially aligned and a second position angularly offset relative to the handle;
   c. a leaf spring defining a first end, second end and spring body; said first end bonded to said neck member, said spring body configured to engage the handle member to provide biasing resistance; and
   d. an adjustable member for engaging the leaf spring at various points along the length of the spring body to provide a variable threshold pressure;
   wherein said leaf spring is operative to normally bias the neck member to the first position and is configured such that the application of pressure to the neck portion beyond the threshold pressure facilitates movement of the neck portion from the first position to the second position.

8. The flexible neck toothbrush of claim 7 wherein said neck member is angularly offset relative to the handle member at an angle in the range from 1 degree to 45 degrees when in the second position.

9. The flexible neck toothbrush of claim 7 wherein said neck member defines a distal end and a proximal end, said distal end including said dental brush and said proximal end including a pivotal connection to said handle member.

10. The flexible neck toothbrush of claim 8 wherein said threshold pressure is the pressure upon the dental brush that causes deflection of the leaf spring.

11. The flexible neck toothbrush of claim 7 wherein said threshold pressure is the pressure upon the dental brush that causes deflection of the leaf spring.

12. The flexible neck toothbrush of claim 7 wherein said handle member defines a distal end and a proximal end, said distal end including a pivotal connection to said neck member.

13. An ergonomic toothbrush having a flexible neck and adaptively designed handle to prevent tooth abrasion and gum damage comprising:
   a. a handle member having a distal end and a proximal end, said distal end of said handle member including a cavity
   b. a neck member incorporating a dental brush, said neck member pivotally connected handle member, said neck member movable between a first position wherein the handle member and neck member are substantially aligned and a second position angularly offset relative to the handle; and
   c. a leaf spring defining a first end, second end and spring body; said first end bonded to said neck member, said second end to be received into the cavity of the handle member, said spring body configured to engage the inner surface of the open cavity of the handle member to provide biasing resistance;
   wherein said leaf spring is operative to normally bias the neck member to the first position and is configured such that the application of pressure to the neck portion beyond a prescribed threshold facilitates movement of the neck portion from the first position to the second position; and
   wherein said prescribed threshold pressure is the pressure upon the dental brush that causes deflection of the leaf spring.

14. The flexible neck toothbrush of claim 13 wherein movement of the neck member about the pivotal connection translates to movement of the leaf spring within the cavity.

15. The flexible neck toothbrush of claim 13 further comprising a protective sheath operatively configured to envelope the distal end of said handle member and the first end of said leaf spring bonded to said neck member.

16. The flexible neck toothbrush of claim 13 wherein said cavity is at least partially filled with a rheostatic fluid.

17. The flexible neck toothbrush of claim 13 wherein said cavity incorporates a rheostatic sponge.

* * * * *